United States Patent [19]
Nappa et al.

[11] Patent Number: 5,866,729
[45] Date of Patent: Feb. 2, 1999

[54] MANUFACTURE OF 1, 1-DIFLUOROETHANE

[75] Inventors: Mario Joseph Nappa, Newark, Del.; William Robert Williams, New Fairfield, Conn.

[73] Assignee: E. I. du Pont de Nemours and Company, Wilmington, Del.

[21] Appl. No.: 778,440

[22] Filed: Jan. 2, 1997

[51] Int. Cl.[6] .................................................. C07C 17/08

[52] U.S. Cl. .......................................... 570/168; 570/166

[58] Field of Search ..................................... 570/168, 166

[56] References Cited

U.S. PATENT DOCUMENTS

| | | | |
|---|---|---|---|
| 2,495,407 | 1/1950 | Chapman et al. | 570/168 |
| 3,862,995 | 1/1975 | Martens et al. | 570/168 |

*Primary Examiner*—Alan Siegel

[57] ABSTRACT

A process for the selective and high yield preparation of 1,1-difluoroethane ($CHF_2$—$CH_3$, HFC-152a) from chloroethene and anhydrous hydrogen fluoride is disclosed. The process involves the reaction of chloroethene with anhydrous hydrogen fluoride in a liquid phase between the temperatures of 30° and 160° C. in the presence of a tin catalyst and at least one compound selected from the group consisting of alkali metal halides and saturated halogenated hydrocarbons.

10 Claims, 1 Drawing Sheet

MANUFACTURE OF 1,1-DIFLUOROETHANE

FIELD OF THE INVENTION

The present invention relates to processes for the selective and high yield preparation of 1,1-difluoroethane, and more particularly, to such processes which comprise contacting chloroethene with hydrogen fluoride in a liquid phase while in the presence of a tin catalyst, and at least one of an alkali metal halide, and a saturated halogenated hydrocarbon.

BACKGROUND OF THE INVENTION

Golubev et al., in U.S.S.R. Inventor Certificate No. 341,788, disclose a liquid phase process for producing 1,1-difluoroethane (HFC-152a) by reacting chloroethene with hydrogen fluoride (HF) while in the presence of tin tetrachloride ($SnCl_4$).

Komatsu et al., in European Patent EP 187,643, disclose a process for manufacturing hydrofluorocarbons (HFCs) by reacting hydrochlorocarbons (HCCs) with HF while in the presence of a tin catalyst and an additive chosen from compounds containing oxygen or nitrogen.

Komatsu et al., in U.S. Pat. No. 4,766,258, disclose a process for the manufacture of HFCs and hydrochlorofluorocarbons (HCFCs) by allowing HCCs to react with anhydrous HF in the presence of a tin catalyst and an additive chosen from compounds containing oxygen or nitrogen.

Franklin et al., in U.S. Pat. No. 4,968,850, disclose a process for the preparation of HFCs and HCFCs by allowing an unsaturated HCC to react with HF in a liquid phase in the presence of a tin catalyst and an organophosphorous additive.

Komatsu et al., in Japanese Kokai publication number SHO 62[1987]-246528, disclose a process for the manufacture of HFCs and HCFCs characterized by allowing a hydrogen-containing halogenated hydrocarbon to react with HF in a liquid phase in the presence of the reaction product from a compound acting as a base in HF, a tin catalyst, and HF.

Pennetreau et al., in European patent application EP 637,579, disclose a method for the preparation of either 1-chloro-1-fluoroethane (HCFC-151a) or HFC-152a by reaction of chloroethene with HF in the presence of a metal catalyst and an organic solvent composed of at least one saturated halogenated hydrocarbon.

1,1-Difluoroethane, hereinafter referred to as HFC-152a or 152a, is a compound of considerable utility. It may be used either alone or in blends with other materials as a refrigerant, blowing agent, propellant, cleaning agent, or as an intermediate for other fluorocarbon compounds, such as fluoroethene. HFCs such as HFC-152a are environmentally acceptable replacements for chlorofluorocarbons (CFCs), since they have no known effect on the earth's stratospheric ozone.

Processes for preparing HFCs and HCFCs from HCCs and HF by metal mediated halogen exchange have found wide industrial utility. The overall process is one in which carbon to chlorine bonds of the HCC are broken and carbon to fluorine bonds are formed in their place. The metal acts in a catalytic capacity leading to a more productive exchange process requiring milder reaction conditions. HFC-152a has been manufactured in this manner using liquid and gas phase processes. The literature reveals that HFC-152a has been prepared by allowing chloroethene to react with HF in the presence of salts of various oxidized metals such as tin(IV), titanium(IV), antimony(III), and antimony(V).

Intermediates in the conventional procedures in which HFC-152a is prepared from chloroethene comprise 1-chloro-1-fluoroethane (HCFC-151a, or 151a) and 1,1-dichloroethane (HCC-150a, or 150a). Byproducts of such conventional procedures include an assortment of oligomeric and polymeric materials; low molecular weight halogenated dimers and oligomers through higher molecular weight halogenated polymers taking the form of oils, tars, and dark carbonaceous solids. These byproducts are typically higher molecular weight, e.g., predominately 50,000, with standard weight fraction distribution from 2,000 to 75,000 number averaged molecular weight, branched, polymeric, halogenated hydrocarbons, which may contain metal species acquired from catalyst and other additives, if present. Such higher molecular weight materials can be formed by polymerization of lower molecular weight dimers, trimers, and oligomers with themselves or with the halogenated carbon-containing reagents and their fluorinated adducts. These byproducts are detrimental to the exchange process as they interfere with catalyst activity, reduce reactor volume, decrease the yield of HFC-152a, and are a disposal concern.

Modification of the metal catalyst through addition of compounds which are inert to fluorination but reactive with the metal species in HF, leads to catalysts with different properties from the parent. The ideal additive for the exchange process is one which minimizes byproduct formation while enhancing the reaction rate and increasing selectivity towards the desired product.

Conventional processes for making HFC-152a are undesirable due to the high amounts of tars produced. The inventive process solves the problems associated with conventional processes by reducing the tar formation rates.

SUMMARY OF THE INVENTION

The present invention is a process for producing HFC-152a comprising providing a liquid phase containing chloroethene, HF, tin catalyst, at least one compound selected from the group consisting of alkali metal halide and saturated halogenated hydrocarbon; heating the mixture; and isolating the HFC-152a formed.

The reaction components may be charged to a reaction vessel in any order, but preferably, the vessel is first charged with tin catalyst, HF, alkali metal halide, and saturated halogenated hydrocarbon. The temperature of this mixture is maintained from 30° C. to 160° C. over the reaction period. During this period, chloroethene is added and is converted to HCFC-151a under the reaction conditions. This HCFC-151a then undergoes fluorine for chlorine halogen exchange under the reaction conditions and product HFC-152a distills out of the reaction mixture.

The process of the present invention can be operated as a batch process. It is perferrable to operate a continuous process by the continuous addition of HF, tin catalyst, alkali metal halide, and saturated halogenated hydrocarbon to the reaction vessel along with chloroethene accompanied by the removal of HFC-152a and HCl.

Analysis of this process reveals high and selective conversion of chloroethene to HFC-152a while minimizing the amounts of oligomeric and polymeric byproducts, i.e., molar yields of at least 80%, usually at least 85% of HFC-152a; and where HFC152a comprises at least 90%, preferably at least 95% of the effluent.

DETAILED DESCRIPTION

Figure 1:
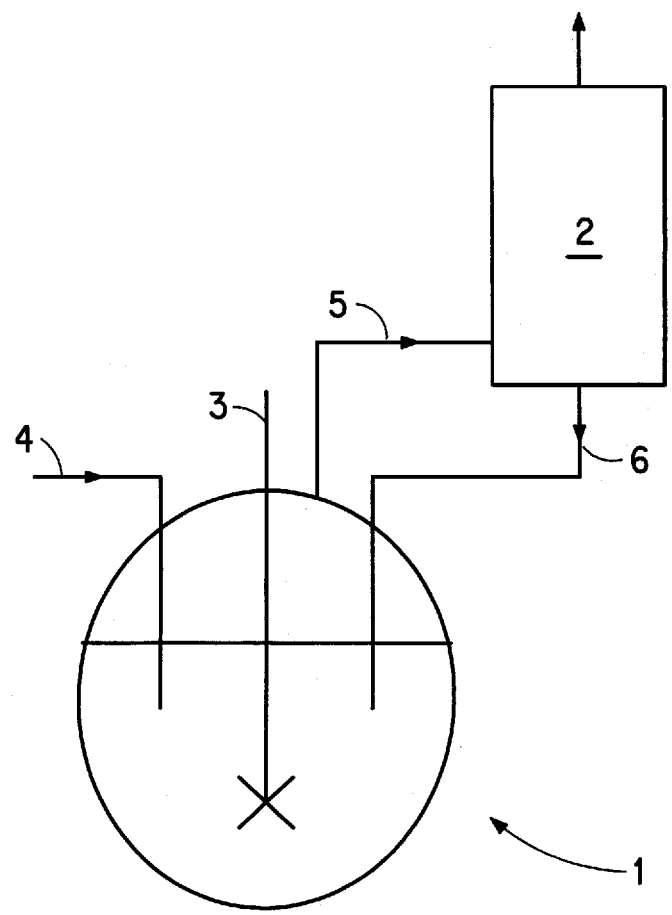
FIG. 1 is a schematic drawing of one embodiment of the process of this invention.

This invention is a process for the selective and high yield synthesis of HFC152a from chloroethene while minimizing the formation of byproducts. The process comprises: providing a mixture comprising chloroethene, HF, at least one tin catalyst, and at least one compound selected from the group consisting of alkali metal halide and saturated halogenated hydrocarbon, heating the mixture, and isolating the HFC-152a formed. Results obtained in this study are summarized in Tables 1 and 2, and reveal the benefits of employing alkali metal halide and saturated halogenated hydrocarbon in the tin(IV) mediated synthesis of HFC-152a from chloroethene and HF. Employing the foregoing embodiments of the invention leads to a marked increase in selectivity for formation of HFC-152a over HCFC-151a; increased molar yields of HFC-152a from chloroethene, and decreased amounts of oligomeric and polymeric byproducts.

Tin catalysts for use in the process of the present invention are selected from the families of tin halides, tin oxyhalides, and organotins. Of the three families, the tin halides are preferred, and of the tin halides, tin(IV) chloride ($SnCl_4$, stannic chloride) is most preferred. Other acceptable tin(IV) halides include $SnBr_4$ and the series of $SnCl_3F$, $SnCl_2F_2$, $SnClF_3$, and $SnF_4$; such species as are generated when $SnCl_4$ is allowed to react with HF. Of the tin oxyhalides, compounds such as $SnCl_2O$, $SnF_2O$, and SnClFO are acceptable. For the purpose of the present invention, organotins are compounds in which the tin atom is bonded to from one to four carbon atoms. Organotin compounds such as tetramethyl tin ($Sn(CH_3)_4$), oxydiethyl tin ($OSn(C_2H_5)_2$), and dichlorodimethyl tin ($SnCl_2(CH_3)_2$) are acceptable.

Alkali metal halides for use in the process of the present invention are of the general empirical formula MX; where M is a group IA alkali metal (where group IA pertains to the said group in the standard periodic table of the elements, such as that represented upon the inner front cover of Lang's Handbook of Chemistry, fourteenth edition, John A. Dean Ed., McGraw Hill, Inc., 1992). Specifically, the metal M may be lithium, sodium, potassium, rubidium, or cesium, and X is a group VIIA halogen such as fluorine, chlorine, bromine, or iodine. Of the alkali metal halides, compounds such as NaCl, KF, KCl, and NaF are preferred; NaCl is most preferred.

The quantity of at least one alkali metal halide that may be used in the process of the present invention is between 0.001 mole to 2 moles per mole of tin catalyst. Preferably, the process is carried out using between 0.1 mole to 1.5 moles of at least one alkali metal halide per mole of tin catalyst.

In one aspect of the invention, one or more of the aforementioned alkali metal halides and tin catalysts can be combined prior to being contacted with chloroethene. For example, NaCl and $SnCl_4$ are premixed, e.g., a suspension NaCl/$SnCl_4$. The premixed alkali metal halide/tin catalyst combination can be employed in any suitable batch or continuous process described herein.

Saturated halogenated hydrocarbons for use in the process of the present invention are selected from the general family $CX^1X^2X^3X^4$, wherein at least one of $X^1$ through $X^4$ is chlorine, and wherein the remainder of $X^1$ through $X^4$ substituents are identical or different and are selected from the group consisting of H, F, Cl, Br, or $C_yZ_{(2y+1)}$, wherein substituents Z are identical or different and are selected from the group consisting of H, F, Cl, or Br, and y is an integer from 1 to 6. The saturated halogenated hydrocarbons of the present invention are preferrably methylene chloride ($CH_2Cl_2$), 1,2-dichloroethane ($CH_2Cl$—$CH_2Cl$), 1,1-dichloroethane ($CHCl_2$—$CH_3$, HCC-150a), 1-chloro-1-fluoroethane ($CHFCl$—$CH_3$, HCFC-151a), and 2,2-dichloro-1,1,1-trifluoroethane ($CF_3$—$CHCl_2$, HCFC-123). The saturated halogenated hydrocarbon may be charged to the reactor as one or more pure compounds or in any mixture composed of several compounds.

The quantity of at least one saturated halogenated hydrocarbon used in the process of the present invention may be from about 0.001 mole to 5 moles per mole of tin catalyst. In the event such a saturated halogenated hydrocarbon is used in the process of the present invention, the process is preferably carried out using from about 0.1 mole to 3 moles saturated halogenated hydrocarbon per mole of tin catalyst; and most preferably from about 0.5 to 1.5 moles per mole of tin catalyst.

Table 1 summarizes results obtained, further reported in the Examples, by operating one aspect of the inventive process. Table 1 illustrates the benefits of employing an alkali metal halide in the tin(IV) mediated synthesis of HFC-152a from chloroethene and HF. Holding all other process variables constant and increasing the mole ratio of alkali metal halide to tin catalyst from 0 to 1 causes a corresponding increase in the HFC-152a/HCFC-151a mole ratio. An increase in the mole ratio of alkali metal halide to tin catalyst may be accompanied by an increase in the molar yield of HFC-152a, and a decrease in the weight percent of tar formation. When the mole ratio of alkali metal halide additive to tin catalyst employed in the present process is greater than 1, the process can be inhibited thereby causing a decrease in the HFC-152a/HCFC-151a product ratio and an increase in tar formation. If the inventive process is operated at a mole ratio of alkali metal halide to tin catalyst of at least about 2, then the process performance can become relatively less effective in comparison to a process operating without alkali metal halide. Thus, the window for most effectively operating the present process is relatively broad. That is, a beneficial effect is observed when employing any mole ratio of alkali metal halide to tin catalyst between and including greater than from about 0 to at least about 1.5; typically from about 0.7 to about 1.3.

TABLE 1

Summary of Experimental Results-Effect of Alkali Metal Halide to Tin Catalyst Mole Ratio on Product Distribution and Tar Formation

| Alkali Metal Halide | Mole Ratio of Alkali Metal Halide to Tin Catalyst | Product Mole Ratio; HFC-152a to HCFC-151a | Mole % Yield HFC-152a | Weight % Tars | Example |
|---|---|---|---|---|---|
| None | — | 41 | 85 | 2.3 | C1 |
| None | — | 44 | 87 | 2.0 | C2 |
| KF | 0.15 | 48 | 100 | 1.0 | 1 |
| KF | 0.30 | 58 | 100 | 0.7 | 2 |

TABLE 1-continued

Summary of Experimental Results-Effect of
Alkali Metal Halide to Tin Catalyst Mole Ratio on
Product Distribution and Tar Formation

| Alkali Metal Halide | Mole Ratio of Alkali Metal Halide to Tin Catalyst | Product Mole Ratio; HFC-152a to HCFC-151a | Mole % Yield HFC-152a | Weight % Tars | Example |
|---|---|---|---|---|---|
| KF | 0.60 | 68 | 100 | 0.4 | 3 |
| KF | 1.00 | 78 | 88 | 0.2 | 5 |
| KCl | 1.00 | 96 | 87 | 0.1 | 6 |
| NaCl | 1.00 | 105 | 85 | 0.2 | 7 |
| NaF | 1.00 | 99 | 88 | 0.3 | 8 |
| KF | 1.90 | 21 | 96 | 4.9 | 4 |

Holding all other process variables constant and adding an amount of saturated halogenated hydrocarbon such as HCFC-123 equimolar with tin catalyst, as is described in Example 18, yields a process in which (versus the comparative case) the mole ratio of HFC-152a/HCFC-151a is increased 28-fold, and the weight of polymeric byproducts formed is decreased by 51%. Holding all other process variables constant and adding both HCFC-123 and KF in amounts equimolar with tin catalyst as in Example 20, yields a process in which (versus the comparative case) the molar yield of HFC-152a increases by 9%, the mole ratio of HFC-152a/HCFC-151a is increased 30-fold, and the weight of polymeric byproducts formed is decreased by 94%.

Study of this embodiment of the present invention, as summarized in Table 2, revealed that a wide variety of saturated halogenated hydrocarbons may be used, with or without an alkali metal halide, to obtain benefits in the tin(IV) catalyzed preparation of HFC-152a from chloroethene and HF. The increased product selectivity coupled with the increased yield (decreased tar formation), along with the possibility of employing a wide variety of additives provides a commercially attractive process.

In one aspect of the invention, the process is performed in a batch operation. Any suitable autoclave, such as a 450 cc Parr® Series 4560 Mini Reactor constructed of Hastelloy C®, is provided. The autoclave is typically fitted with a turbine impeller for agitating the liquid contents of the autoclave, a septum port for introducing or withdrawing liquids from the autoclave by syringe or cannula technique, valved ports for introducing or withdrawing gaseous or liquid materials, a jacketed 0.25 inch diameter tube reflux condenser topped with a valved takeoff port, and an external heating jacket. The inventive batch method may generally be carried out on any scale desired. The equipment and associated feed lines, effluent lines, and associated units should be constructed of materials resistant to HF and HCl. Typical materials of construction, well-known to the fluorination art, include stainless steels and high nickel alloys, such as Monel® nickel-copper alloys, Hastelloy® nickel-based alloys, and Inconel® nickel-chromium alloys.

A dry autoclave is transferred into a dry-box and the desired amount of at least one tin catalyst, at least one compound selected from the group consisting of alkali metal halide and saturated halogenated hydrocarbon, are charged

TABLE 2

Summary of Experimental Results-Effect of Saturated
Halogenated Hydrocarbon and Alkali Metal Halide to
Tin Catalyst Mole Ratio on Product Distribution and Tar Formation

| Saturated Halogenated Hydrocarbon and Alkali Metal Halide Employed | Mole Ratio of Saturated Halogenated Hydrocarbon and Alkali Metal Halide to Tin Catalyst | Product Mole Ratio; HFC-152a to HCFC-151a | Molar Yield HFC-152a | Weight % Tars | Example Number |
|---|---|---|---|---|---|
| None | — | 41 | 85 | 2.3 | C1 |
| None | — | 44 | 87 | 2.0 | C2 |
| $CH_2Cl_2$ | 0.5 | 111 | 87 | 2.3 | 11 |
| $CH_2Cl_2$ | 1.0 | 470 | 94 | 1.8 | 12 |
| $CH_2Cl_2$ | 1.0 | 1030 | 85 | 1.7 | 17 |
| HCFC-123 | 1.0 | 1170 | 82 | 2.0 | 19 |
| HCFC-123 | 1.5 | 358 | 90 | 1.1 | 20 |
| HCFC-123 | 3.0 | 4 | 72 | 0.28 | 13 |
| $ClCH_2$—$CH_2Cl$ | 0.6 | 53 | 87 | 2.5 | 14 |
| KF $CH_2Cl_2$ | 0.7 (KF) 0.7 ($CH_2Cl_2$) | 404 | 95 | 0.3 | 16 |
| KF HCFC-123 | 1.0 (KF) 1.0 (123) | 1260 | 95 | 0.1 | 20 |
| KF HCFC-123 | 0.5 (KF) 0.5 (123) | 340 | 90 | 0.3 | 21 |
| NaF HCFC-123 | 1.1 (NaF) 1.0 (123) | 1267 | — | — | 22 | to the autoclave. The tin catalysts are normally loaded into the autoclave while within a dry-box in order to minimize any reaction between the tin compounds and moisture present in the air.

The autoclave is sealed, and removed from the drybox. A port of the autoclave is then attached to a vacuum pump and the lower portion cooled by being placed into liquid nitrogen, and the autoclave is evacuated. By establishing a vacuum in the autoclave, potentially deleterious air is removed thereby permitting more efficient transfer of gaseous HF. Liquid nitrogen facilitates transfer of HF by condensing gaseous HF. The autoclave is then attached to an HF cylinder and the desired amount of HF is vacuum transferred into the autoclave.

The quantities of chloroethene, HF, and tin catalyst present in the autoclave may vary over a broad range of effective operation. The quantity of materials used in the process of the present invention is generally between about 0.1 to at least about 10 (kg chloroethene fed/hour)/kg catalyst, usually about 0.2 (kg chloroethene fed/hour)/kg catalyst when the tin catalyst comprises $SnCl_4$. The initial amount of catalyst charged with HF is generally between about 5 to at least about 35 weight %, for example, $SnCl_4$ in HF, normally from about 10 to about 20 weight % tin catalyst in HF.

After the starting materials are introduced into the sealed autoclave, the autoclave is then detached from the vacuum and HF sources, and allowed to warm to ambient temperature. The autoclave is then heated to a temperature of about 30° C. to about 160° C., normally from about 50° C. to about 95° C., and the total pressure within the autoclave is maintained between about 60 kPa and about 3000 kPa, normally about 345 kPa. The pressure within the autoclave can be maintained by using any suitable means such as a back pressure regulator.

Gaseous chloroethene is then added to the autoclave at a rate that varies as a function of the amount of HF and tin catalyst within the autoclave, e.g., adding chloroethene at a rate of about 10 to about 100 sccm (about 0.01 to about 0.5 kg/hr/kg-catalyst). A gaseous effluent exiting a reflux condenser, which is in fluid communication with the autoclave, is collected by condensation and monitored. The composition of the effluent is monitored by using an on-line gas chromatograph (GC). After the addition of chloroethene has ceased, the autoclave is vented of excess gaseous and liquid materials by a nitrogen purge. The solid contents of the autoclave are then removed, drowned with water and filtered. The filtrate is rinsed with 10% aqueous hydrochloric acid, water, and dried in a vacuum oven to a constant weight. The composition of the dried mass is also analyzed in order to determine the amount of tar that was formed.

While the aforementioned batch process can be employed, a continuous process is particularly desirable from an industrial standpoint. Referring now to FIG. 1, FIG. 1 is a schematic diagram for a continuous HFC-152a manufacturing process. A reactor 1 is in fluid communication with a reflux column 2. Typically, the reflux column 2 will have a reflux ratio of between about 2 to about 20 when operated at a pressure of about 345 to about 3000 kPa and a temperature of about 30° C. to about 160° C. Predetermined amounts (as previously discussed for batch process) of HF, at least one catalyst, at least one compound selected from the group consisting of alkali metal halide and saturated halogenated hydrocarbon are added to the reactor 1. The contents of the reactor 1 are agitated by using a dual bladed agitator with pump down action 3, heated, and brought to reflux at the desired operating temperature/pressure. When the desired operating conditions have been established, HF and chloroethene are fed continuously to the reactor via one or more feed lines 4. Gas exits from the reactor 1 and is transported to the reflux column 2 via one or more feed lines 5. The gas stream leaving the reflux column 2 typically consists essentially of HFC-152a and HCl, e.g., about 60 to about 70 wt % HFC-152a. A liquid return line 6 is connected to the bottom of the reflux column 2. Line 6 returns high boiling intermediates such as 1,1-dichloroethane and HCFC-151a, among others, and any HF to reactor 1. The gas stream leaving the reactor 1 or reflux column 2 can be purified by any suitable manner such as by using two conventional distillation steps (not shown in FIG. 1). The first distillation step removes HCl. The second distillation step removes any unreacted intermediates and HF that are recovered and, if desired, recycled to reactor 1.

Similar to operating a batch process as discussed earlier, the continuous production equipment and its associated feed lines, effluent lines and any handling units should be constructed of materials resistant to HF and HCl.

While the previous description has placed particular emphasis upon making a product stream wherein HFC-152a is the major component, the inventive process can also be operated in a manner which produces other desirable compounds. That is, the present process can produce HFC-152a alone or co-produced with one or more of HCFC-141b (1,1-dichloro-1-fluoroethane), HCFC-142b (1-chloro-1,1-difluoroethane), HFC-143a (1,1,1,1-trifluoroethane), among others, e.g., from a hydrochlorocarbon such as 1,1-dichloroethene. The co-produced product can be recovered and employed as a useful mixture, or separated into its individual components.

The following examples are provided for the purpose of further illustrating the present invention without limiting the invention as defined in the appended claims. In the following Examples, chloroethene was supplied by Fluka Incorporated, Ronkonkoma, N.Y., HF was supplied by Air Products (Allentown, Pa.) and noniodized NaCl was supplied by Morton Salt, Chicago, Ill. All compounds employed in the following Examples were commercially available.

EXAMPLES

Example 1—KF Additive

Commercially available tin tetrachloride ($SnCl_4$, 37.5 g, 0.144 mol) and potassium fluoride (KF, 1.25 g, 0.0215 mol) were added to a Hastelloy C® 450 cc Parr® Series 4560 Mini Reactor that was housed within a dry box. The reactor head, which was equipped with a 0.25 inch tube reflux condenser, was attached to the autoclave, removed from the drybox and connected to a stainless steel vacuum line. The base of the reactor was immersed in liquid nitrogen. HF (150 g, 7.5 mol) was vacuum transferred into the reactor. The liquid nitrogen cooling bath was removed, the temperature of the reactor was raised by using external heating until the internal temperature was about 25° C., and cooling water (3.7° C.) was circulated through the condenser. A heating jacket was placed around the reactor, and the internal temperature of the reactor was increased to about 50° C. while maintaining the internal pressure at about 345 kPa by using a back pressure regulator.

The flow of chloroethene (44.1 standard cubic cm/minute or sccm, $7.4 \times 10^{-7}$ $m^3$/sec) and methane (9.8 sccm, $1.6 \times 10^{-7}$ $m^3$/sec) were begun. In all of the Examples except 10, 24, and comparative examples 3 and 4, methane was introduced into the reactor as a standard for the gas chromatograph as well as diluent to assist in removing material from the reactor.

Gaseous effluent from the reactor was monitored every hour for the approximately 16.7 hours of chloroethene addition. The molar yield of HFC-152a based on the chloroethene fed was measured to be about 97%. The HFC-152a was found by on-line GC to be about 100% of the effluent. The ratio of HFC152a/HCFC-151a (averaged from the $4^{th}$ to the $16^{th}$ hour of the experiment) as measured by GC was about 48. At the end of the run, the reactor was vented to atmospheric pressure to drive off volatiles, e.g., HF and organics. Further removal of volatiles was assisted by using a nitrogen purge. Any solids remaining in the autoclave were drowned in water and filtered on a Teflon® membrane filter. The filtrate was washed with 10% HCl and then with water, and dried at a temperature of about 115° C. in a convection oven to constant weight. The tars formed over this run averaged about 1.00 g per 100 g chloroethene fed.

Comparative Example 1—No Alkali Metal Halide or Saturated Halogenated Hydrocarbon Additive The apparatus, procedure, and materials used for this Comparative Example were substantially identical to those discussed for Example 1; with the exception that no alkali metal halide additive was used.

The molar yield of HFC-152a based on the chloroethene fed was measured to be about 85%. The HFC-152a product as measured by an on-line GC was found to be about 98% of the effluent. The ratio of HFC-152a/HCFC-151a (averaged from the $4^{th}$ to the $17^{th}$ hour of the experiment) was measured to be about 40. After approximately 18 hours of operation, the reactor was cooled and vented to atmospheric pressure to drive off volatiles, e.g., HF and organics. The remainder was worked up as in Example 1. The tars formed over this run averaged about 2.30 g per 100 g chloroethene fed.

Table 3—Examples 1 through 9 and Comparative Examples 1 and 2

Examples 2 through 9 employed a procedure substantially identical to that disclosed in Example 1, and Comparative Example 2 employed a procedure substantially identical to Comparative Example 1. In the case of Examples 5, 6, 7, 8 and Comparative Example 2, aliquots of reactor mass of about 20 to 70 grams were taken immediately at the end of the run and analyzed for the presence of elemental tin. Results are reported in Table 3. Process variables which were altered from those of Example 1, and the reaction products, are also reported in Table 3. Process variables which remained constant throughout the runs are listed in the Note following Table 3.

TABLE 3

Alkali Metal Halides as Additives

| Ex[a] | Alkali Metal Halide, Mole Ratio Alkali Metal Halide to Tin Catalyst | Chloroethene Addition Rate (sccm)[b] | Rxn. Time (hr) | % Molar Yield[e] 152a, (% purity effluent) | 152a/151a Product Mole Ratio | Grams Tar per 100 g Chloroethene Fed | Weight % Tin in Reactor Mass |
|---|---|---|---|---|---|---|---|
| 1 | KF, 0.15 | 44.1 | 16 | Quantitative | 48 | 1.0 | — |
| 2 | KF, 0.30 | 42.0 | 17 | Quantitative | 58 | 0.67 | — |
| 3 | KF, 0.60 | 42.0 | 16.3 | Quantitative | 68 | 0.41 | — |
| 4[a] | KF, 1.9 | 42.0 | 17 | 96 (93) | 21 | 4.86 | — |
| 5 | KF, 1.0 | 50.2 | 15.5 | 88, (99) | 78 | 0.15 | 13.4 |
| 6 | KCl, 1.0 | 50.2 | 15.5 | 87, (99) | 96 | 0.14 | 14.4 |
| 7 | NaCl, 1.0 | 50.1 | 15.5 | 85, (99) | 105 | 0.21 | 14.4 |
| 8[c] | NaF, 1.0 | 50.2 | 15.5 | 88, (99) | 99 | 0.29 | 11.1 |
| 9 | NaCl, 0.50 | CCl$_3$CH$_3$ 12.2 Chloroethene 25.3 | 14 | 143a = 68.4 142b = 29.9 152a = 98.3 | 143a/142b = 2.3 152a/151a = 49 | 0.70 | — |
| C1 | None | 49.2 | 16.5 | 85, (98) | 41 | 2.3 | — |
| C2 | None | 49.2 | 16.3 | 87, (98) | 44 | 2.03 | 5.4 |
| 10[d] | KF, 0.60 | d | d | d | 59 | 3.5 | — |
| C3[d] | None | d | d | d | 11 | 7.12 | — |

Table 3 Notes
[a] All examples (except for 4, 10 and C3) used 0.144 mole SnCl$_4$. Example 4 used 0.0768 mole SnCl$_4$. All examples (except for 10 and C3) used 7.5 mole of anhydrous HF. All examples were carried out at 50° C. and 345 kpa for the time specified in the "Rxn. Time (hrs)" column.
[b] sccm = standard cubic centimeters/minute
[c] See experimental description which follows Amounts of materials were the same but the addition order changed.
[d] See following experimental description for example 10 and comparative example 3. The procedure was slightly different than that of Examples 1–9 and comparative examples 1 and 2.
[e] Yield of 152a is calculated by reference to the internal standard methane.

Examples 5–8, and Comparative Example 2, were carried out as described earlier with the exception that at the end of the run, an evacuated cylinder was attached to a reactor dip tube and a portion of the reactor mass was removed for analysis of elemental tin. The results of these Examples were reported earlier in Table 3.

Example 5—KF Additive

The apparatus, procedure, and materials used for this Example were substantially identical to those described earlier in Example 1.

Potassium fluoride (KF, 8.37 g, 0.144 mol) was charged to the reactor along with tin tetrachloride. Chloroethene was added at a rate of 50.2 sccm ($8.37 \times 10^{-7}$ m$^3$/sec) with internal standard methane being added at rate of 9.8 sccm ($1.63 \times 10^{-7}$ m$^3$/sec). The gaseous effluent was monitored every hour during the approximately 15.5 hours of chloroethene addition. The molar yield of HFC-152a based on the chloroethene fed was about 88% by GC comparison to methane. The HFC-152a was analyzed by an on-line GC to be about 99% by GC analysis of the effluent. The ratio of HFC-152a/HFC- 151a (averaged from the 4$^{th}$ to the 15$^{th}$ hour of the experiment) as measured by GC was about 78. At the end of the run and immediately after the agitator had stopped, an approximately 39.3 g sample of the reactor mass was removed through the dip tube of the reactor by temporarily connecting an evacuated cylinder to the lines normally used for feeding chloroethene and methane. The sample was analyzed by X-ray fluorescence and found to contain about 13.4% Sn by weight. The reactor was vented to atmospheric pressure to remove any volatiles, e.g., HF and organics. The remainder was worked up as in Example 1. The tars formed over this run averaged about 0.15 g per 100 g chloroethene fed.

Example 8—Late Charge of NaF Additive

Tin tetrachloride (SnCl$_4$, 37.5 g, 0.144 mol) was added to a Hastelloy C® 450 cc Parr® Series 4560 Mini Reactor that was housed within a dry box. A reactor head, which was equipped with a 0.25 inch tube reflux condenser, was attached to the Mini Reactor. The reactor was removed from the drybox and connected to a stainless steel vacuum line. The base of the reactor was immersed within liquid nitrogen, and HF (100 g, 5.0 mol) was vacuum transferred into the reactor. The liquid nitrogen cooling bath was removed, the temperature of the reactor raised by using external heating until the internal temperature was about 25° C., and cooling water (3.7° C.) began circulating through a condenser attached to the reactor head. A heating jacket was placed around the reactor, and the internal temperature of the reactor was increased to about 50° C. while maintaining the internal pressure at about 345 kPa by using a back pressure regulator. The contents of the reactor were allowed to react for about two hours under the previously described conditions thereby allowing the SnCl$_4$ catalyst and HF to form a tin chlorofluoride catalyst. After this two hour period, a pressurized solution of NaF (6.00 g, 0.143 mol) in HF (50 g, 2.5 mol) was injected into the catalyst solution. The resultant mixture was stirred for about 15 minutes, at which time the flow of chloroethene (50.2 sccm, $8.37 \times 10^{-7}$ m$^3$/sec) and internal standard methane (9.4 sccm, $1.57 \times 10^{-7}$ m$^3$/sec) were begun. The gaseous effluent exiting the reactor was analyzed every hour for the 15.5 hours of chloroethene addition. The molar yield of HFC-152a based on the chloroethene fed was determined by GC to be about 88% by comparison to the methane standard. The HFC-152a was measured by on-line GC to be about 99% of the effluent. The ratio of HFC-152a/HCFC-151a (averaged from the 4$^{th}$ to the 15$^{th}$ hour of the experiment) as measured by GC was about 99. At the end of the run, a 20.4 g sample of the reactor mass was taken through a dip tube immediately after the agitator had stopped. The sample was analyzed by X-ray fluorescence to contain about 11.1% Sn by weight as elemental tin. The reactor was vented to atmospheric pressure to remove volatiles, e.g., HF and organics. The remainder was worked up as in Example 1. By gravimetric analysis, it was determined that the tars formed over this run averaged about 0.29 g per 100 g chloroethene fed.

Comparative Example 2—No Alkali Metal Halide or Saturated Halogenated Hydrocarbon Additive The apparatus, procedure, and materials used for this Example were substantially identical to those discussed for Comparative Example 1.

The flow of chloroethene to the reactor was approximately 49.2 sccm ($8.2 \times 10^{-7}$ m$^3$/sec) and internal standard methane was 9.8 sccm ($1.6 \times 10^{-7}$ m$^3$/sec). A gaseous effluent exiting the reactor was monitored every hour during approximately 16.3 hours of chloroethene addition. The molar yield of HFC-152a as based on the chloroethene fed was 87%. The HFC-152a was found by on-line GC to be 98% of the effluent. The ratio of HFC-152a/HCFC-151a (averaged from the 4$^{th}$ to the 16$^{th}$ hour of the experiment), which was measured by using an GC, was 44. At the end of the experiment a 21.6 g sample of the reactor mass was removed from the reactor via a dip tube immediately after the agitator had stopped. The sample was found by X-ray fluorescence to contain about 5.4% Sn by weight as elemental tin. The reactor was vented to atmospheric pressure to remove volatiles, e.g., HF and organics. The remainder was worked up as in Example 1. The tars formed over this experiment averaged about 2.03 g per 100 g chloroethene fed.

Example 9—NaCl Additive—Coproduction of HFC-152a and HFC-143a

The apparatus, procedure, and materials used for this Example were substantially identical to those discussed in Example 1.

Sodium chloride (NaCl, 4.21 g or 0.072 mol) was charged to the reactor along with the tin tetrachloride. HCC-140a (1,1,1-trichloroethane) was added to the reactor at a rate of 12.2 sccm ($2.03 \times 10^{-7}$ m$^3$/sec), chloroethene at a rate of 25.3 sccm ($4.23 \times 10^{-7}$ m$^3$/sec), and internal standard methane at a rate of 10.3 sccm ($1.7 \times 10^{-7}$ m$^3$/sec). The gaseous effluent exiting the reactor was monitored every hour during the 14 hours of continuous addition. The gaseous effluent comprised molar yields of 1,1,1- trifluoroethane (HFC-143a, based on 1,1,1-trichloroethane fed), 1-chloro-1,1-difluoroethane (HCFC-142b, based on 1,1,1-trichloroethane fed), and HFC-152a (based on chloroethene fed) were determined to be about 68.4%, 29.9%, and 98.3%, respectively. The mole ratio of HFC-143a/HCFC-142b (averaged from the 5$^{th}$ to the 14$^{th}$ hour of the experiment) was determined to be about 2.3, and the mole ratio of HFC-152a/HCFC-151a was determined to be about 49. At the end of the experiment, the reactor was vented to atmospheric pressure to remove volatiles, e.g., HF and organics. The remainder was worked up as in Example 1. The tars formed over this run averaged about 0.70 g per 100 g chloroethene fed.

Example 10—KF Additive

Tin tetrachloride (SnCl$_4$, 100 g, 0.383 mol) and potassium fluoride (KF, 13.4 g, 0.230 mol) were added to a Hastelloy C® 600 cc Parr® Mini Reactor that was housed in a dry box. The reactor head was equipped with two ports for feed or sampling, a reflux column with a port for collecting exiting vapors, and an agitator. The reactor was sealed, the reactor base cooled, and HF (300 g, 15 mol) was transferred into the reactor. The resulting mixture was allowed to digest for approximately 15 hours. The contents of the reactor were then heated to a temperature of about 80° C., and agitation and chloroethene feed began. HF was then introduced into the reactor and the feed rate adjusted so as to maintain a constant weight of material in the reactor. After the HF introduction achieved a constant weight in the reactor and successive on-line GC analyses of the reflux condenser effluent were within experimental error, the process was consider to be at steady state. At an approximately 19.6 g/hr chloroethene feed rate, the following steady state results were measured by using an on-line GC analysis of the reflux condenser effluent: HFC-152a (97.9% by GC peak area integration), chloroethene (0.017%), HCFC-151a (1.7%) and 1,1-dichloroethane (0.2%). The relative molar ratio of HFC-152a/HCFC-151a was found by GC to be about 59. At the end of this experiment, tar solids were obtained substantially in the manner described in Example 1. The tars formed over this experiment averaged about 3.5 g per 100 g of chloroethene fed.

Comparative Example 3—No Alkali Metal Halide or Saturated Halogenated Hydrocarbon Additive The apparatus, procedure, and materials used for this Comparative Example were substantially identical to those described in Example 10.

The initial materials charged into the reactor were tin tetrachloride (140 g, 0.56 mol) and HF (300 g, 15 mol). A steady-state reaction was carried out at a temperature of about 76° C. At an approximately 18.2 g/hr chloroethene feed rate, the following steady state conditions were measured by an on-line GC analysis of the reflux condenser effluent: HFC-152a (89.6% by GC peak integration), chloroethene (about 0%), HCFC-151a (7.8%), and 1,1-dichloroethane (2.4%). The relative ratio of HFC-152a/HCFC-151a was determined by using GC to be about 11. At the end of the experiment, tar solids were obtained substantially in the manner described in Example 1. The tars formed over this run averaged about 7.12 g per 100 g of chloroethene fed.

Example 11—Methylene Chloride as Additive

Tin tetrachloride ($SnCl_4$, 37.5 g, 0.144 mol) and methylene chloride ($CH_2Cl_2$, 6.12 g, 0.0721 mol) were charged to a Hastelloy® C 450 cc Parr® Series 4560 Mini Reactor in a dry box. The reactor head, which was equipped with a 0.25 inch diameter tube reflux condenser, was attached to the reactor; and, then the reactor was removed from the drybox and connected to a stainless steel vacuum line. The base of the reactor was immersed in liquid nitrogen and HF (150 g, 7.5 mol) was vacuum transferred into the reactor. The liquid nitrogen cooling bath was removed, the temperature of the reactor raised using external heating until the internal temperature was near 25° C., and cooling water (3.7° C.) was circulated through the condenser. A heating jacket was placed around the reactor, and the internal temperature of the reactor was brought to 50° C. while maintaining the internal pressure at 345 kPa by use of a back pressure regulator. At this time, flow of chloroethene (50.1 standard cubic centimeter/minute or sccm, $8.35 \times 10^{-7}$ $m^3$/sec) and internal standard methane (9.4 sccm, $1.57 \times 10^{-7}$ $m^3$/sec) were begun. The gaseous effluent was monitored every hour for the 16 hours of chloroethene addition. The molar yield of HFC-152a, based on the chloroethene fed, was measured to be 87%. The HFC-152a was measured by on-line gas chromatography (GC) to be 98% of the effluent. The mole ratio of HFC152a/HCFC-151a (averaged from the $4^{th}$ to the $16^{th}$ hour of the experiment) measured by GC was 111. At the end of the run, the reactor was vented to atmospheric pressure to drive off volatiles (HF and organics). The remainder was worked up as in Example 1. The tars formed over this run averaged 2.31 g per 100 g chloroethene fed.

Examples 12 through 22

Examples 12 through 22 used a procedure identical to that of Example 11 and these examples are summarized in Table 4. The reaction products and process variables which differed from the standard procedure of Example 11 are reported in Table 4, while process variables which were similar to those in Example 11 and remained constant throughout the examples, are listed in the note following Table 4.

Examples 15, 17, 22, and C4 are discussed following Table 4 to clarify the procedure used in these instances versus that of Example 11.

TABLE 4

Alkali Metal Halides and/or Saturated Halogenated Hydrocarbons as Additives

| Ex.[a] | Alkali Metal Halide (moles used, mole ratio to tin catalyst) | Saturated Halogenated Hydrocarbon (moles used, mole ratio to tin catalyst) | Rxn. Time (hr) | Molar % Yield 152a (% purity effluent) | 152a/151a Product Mole Ratio | Grams Tar per 100 g Chloroethene Fed | Weight % Tin in Reactor Mass |
|---|---|---|---|---|---|---|---|
| C1 | — | — | 16.5 | 85 (98) | 41 | 2.30 | — |
| C2 | — | — | 16.3 | 87 (98) | 44 | 2.03 | 5.4 |
| 11 | — | $CH_2Cl_2$, 0.0741, 0.50 | 16.0 | 87 (98) | 111 | 2.31 | — |
| 12 | — | $CH_2Cl_2$, 0.1444, 1.0 | 16.3 | 94 (98) | 470 | 1.85 | — |
| 13 | — | $CF_3$—$CHCl_2$, 0.434, 3.0 | 15.8 | 72 (84) | 4 | 0.28 | — |
| 14 | — | $ClCH_2$—$CH_2Cl$ 0.0902, 0.63 | 16.5 | 87 (8) | 53 | 2.46 | — |

TABLE 4-continued

Alkali Metal Halides and/or Saturated Halogenated Hydrocarbons as Additives

| Ex.[a] | Alkali Metal Halide (moles used, mole ratio to tin catalyst) | Saturated Halogenated Hydrocarbon (moles used, mole ratio to tin catalyst) | Rxn. Time (hr) | Molar % Yield 152a (% purity effluent) | 152a/151a Product Mole Ratio | Grams Tar per 100 g Chloroethene Fed | Weight % Tin in Reactor Mass |
|---|---|---|---|---|---|---|---|
| 15 | — | $CH_2Cl_2$, 0.143, 1.0, $N(CH_3)_3$, 0.092, 0.63 | 16.8 | 91 (99) | 1440 | 0.42 | — |
| 16 | KF, 0.0931, 0.65 | $CH_2Cl_2$, 0.0936, 0.65 | 16.5 | 95 (99) | 404 | 0.28 | — |
| 17 | — | $CH_2Cl_2$, 0.144, 1.0 | 16.8 | 85 (99) | 1030 | 1.66 | 4.46 |
| 18 | — | $CF_3$—$CHCl_2$, 0.144, 1.0 | 15.0 | 82 (99) | 1170 | 1.13 | 1.99 |
| 19 | — | $CF_3$—$CHCl_2$, 0.215, 1.5 | 16.3 | 90 (99) | 358 | 1.12 | 1.92 |
| 20 | KF, 0.146, 1.0 | $CF_3$—$CHCl_2$, 0.145, 1.0 | 15.8 | 95 (100) | 1260 | 0.13 | 14.0 |
| 21 | KF, 0.0714, 0.5 | $CF_3$—$CHCl_2$, 0.072, 0.5 | 16.0 | 90 (100) | 340 | 0.26 | 34.7 |
| Examples C4 and 22 were performed in a 1.4× larger apparatus under continuous steady-state operating conditions. | | | | | | | |
| 4[b] | — | — | | 84.8% purity 152a | 7.5 | — | |
| 2[b] | NaF, 0.404, 1.1 | $CF_3$—$CHCl_2$, 0.383, 1.0 | | 96.3% purity 152a | 1267 | — | |

Table 4 Notes
[a]As in Example 11, Examples 12–22, C1, and C2 used 0.144 mole $SnCl_4$, 7.5 moles HF, and were carried out at 50° C. and 345 kPa. Chloroethene was fed to the reactor at a rate of 50 sccm and post reaction work-up followed the procedure of Example 11.
[b]These examples employed 0.383 mole $SnCl_4$, 14.3 (Example 22) and 20 (Comparative Example C4) moles HF, and were carried out at 93° (Example 22) and 95° C. (Comparative Example C4) in a 600 cc reactor. Detailed procedural description for Examples 22 and C4 follows.

Example 15—Methylene Chloride and Trimethylamine Additives

Tin tetrachloride ($SnCl_4$, 37.5 g, 0.144 mol) and methylene chloride ($CH_2Cl_2$, 12.21 g, 0.143 mol) were charged to a Hastelloy® C 450 cc Parr® Series 4560 Mini Reactor in a dry box. The reactor head, which was equipped with a 0.25 inch diameter tube reflux condenser, was attached and the reactor removed from the drybox and connected to a stainless steel vacuum line. The base of the reactor was immersed in liquid nitrogen and HF (150 g, 7.5 mol) was vacuum transferred into the reactor. After completion of transfer of HF, trimethylamine ($N(CH_3)_3$, 5.40 g, 0.092 mol) was vacuum transferred into the reactor. The liquid nitrogen cooling bath was removed, and the temperature of the reactor was raised using external heating until the internal temperature was near 25° C., and cooling water (3.7° C.) was begun circulating through the condenser. A heating jacket was placed around the reactor, and the internal temperature of the reactor was brought to 50° C. while maintaining the internal pressure at 345 kPa by use of a back pressure regulator. At this time, flow of chloroethene (50.2 standard cubic centimeter/minute or sccm, $8.37 \times 10^{-7}$ $m^3$/sec) and internal standard methane (9.4 sccm, $1.57 \times 10^{-7}$ $m^3$/sec) were begun. The gaseous effluent was monitored every hour for the 16.8 hours of chloroethene addition. The molar yield of HFC-152a, based on the chloroethene fed, was measured to be 91%.

The HFC-152a was measured by on-line gas chromatography (GC) to be 99% of the effluent. The mole ratio of HFC-152a/HCFC-151a (averaged from the 4th to the 16th hour of the experiment) measured by GC was 1440. At the end of the run, the reactor was vented to atmospheric pressure to drive off volatiles (HF and organics). The remainder was worked up as in Example 1. The tars formed over this run averaged 0.42 g per 100 g chloroethene fed.

Example 17—Methylene Chloride as Additive and Weight % Sn Determination in Reactor Mass Tin tetrachloride ($SnCl_4$, 37.5 g, 0.144 mol) and methylene chloride ($CH_2Cl_2$, 12.22 g, 0.144 mol) were charged to a Hastelloy® C 450 cc Parr® Series 4560 Mini Reactor in a dry box. The reactor head, which was equipped with a 0.25 inch diameter tube reflux condenser, was attached and the reactor removed from the drybox and connected to a stainless steel vacuum line. The base of the reactor was immersed in liquid nitrogen and HF (150 g, 7.5 mol) was vacuum transferred into the reactor. The liquid nitrogen cooling bath was removed, and the temperature of the reactor was raised using external heating until the internal temperature was near 25° C., and cooling water (3.7° C.) was begun circulating through the condenser. A heating jacket was placed around the reactor, and the internal temperature of the reactor was brought to 50° C. while maintaining the internal pressure at 345 kPa by use of a back pressure regulator. At this time, flow of chloroethene (50.2 standard cubic centimeter/minute or sccm, $8.37 \times 10^{-7}$ $m^3$/sec) and internal standard methane (9.5 sccm, $1.58 \times 10^{-7}$ $m^3$/sec) used as an internal standard were begun. The gaseous effluent was monitored every hour for the 16.8 hours of chloroethene addition. The molar yield of HFC-152a based on the chloroethene fed was measured to be 85%. The HFC-152a was measured by on-line gas chromatography (GC) to be 99% of the effluent. The mole ratio of HFC-152a/HCFC-151a (averaged from the $4^{th}$ to the $16^{th}$ hour of the experiment) measured by GC was 1030. At the end of the run, a 66.4 g sample of the reactor mass was taken through a dip tube immediately after the agitator was stopped. The sample was found by X-ray fluorescence to contain about 4.46% Sn by weight as elemental tin. The reactor was vented to atmospheric pressure to drive off volatiles (HF and organics). The remainder was worked up as in Example 1. The tars formed over this run averaged 1.66 g per 100 g chloroethene fed.

Example 22—NaF and HCFC-123 as Additives

Tin tetrachloride ($SnCl_4$, 100. g, 0.383 mol), sodium fluoride (NaF, 17.0 g, 0.404 mol), and HCFC-123 ($CF_3$-$CHCl_2$, 58.7 g, 0.383 mol) were charged to a Hastelloy® C 600 cc Parr® Mini Reactor in a dry box. The reactor head was equipped with two ports for feed or sampling, a reflux column with port for collection of exiting vapors, and an agitator. The reactor was sealed, the base cooled, and HF (286 g, 14.3 mol) was charged to the reactor. The resulting mixture was allowed to sit for 15 hours. The contents of the reactor were then heated to 93° C. and agitation and chloroethene feed begun. HF feed was then started and adjusted so as to maintain a constant total weight of material in the reactor. Once this was attained, and once successive on-line GC analyses of the reflux condenser effluent were within experimental error, the process was consider to be at steady state.

At a 19.6 g/hr (0.31 mol/hr) rate of chloroethene feed, the following steady state results were obtained by on-line GC analysis of the reflux condenser effluent: HFC-152a (96.3% by GC peak area integration), chloroethene (0.0%), HCFC-151a (0.1%), 1,1-dichloroethane (0.0%). The relative ratio of HFC-152a/HCFC-151a was measured by GC to be 1267.

Comparative Example 4 (C4)—No Alkali Metal Halide or Saturated Halogenated Hydrocarbon Additive The apparatus, procedure, and materials used for this example were identical to those discussed for Example 23, except that no additives were employed. The following provides the results obtained from this example and discloses the deviations in procedure from Example 23.

The HF charge to the reactor was 400 g (20 mol). At a 19.6 g/br (0.31 mol/br) rate of chloroethene feed, the following steady state results were obtained by on-line GC analysis of the reflux condenser effluent: HFC-152a (84.8% by GC peak area integration), chloroethene (0.1%), HCFC-151a (11.3%), 1,1-dichloroethane (0.8%). The relative ratio of HFC-152a/HCFC-151a was found by GC to be 7.5.

What is claimed is:

1. A process for the manufacture of 1,1-difluoroethane comprising:
   a) providing a liquid phase mixture comprising chloroethene, hydrogen fluoride, a catalyst system comprising at least one tin catalyst selected from the group consisting of a tin halide, a tin oxyhalide and an organo tin, and at least one compound selected from the group consisting of an alkali metal halide and a saturated halogenated hydrocarbon of the formula $CX^1X^2X^3X^4$, wherein at least one of $X^1$ through $X^4$ is chlorine and the remainder are each selected from the group consisting of hydrogen, fluorine, bromine and $C_{(y)}Z_{(2y+1)}$, wherein Z is selected from the group consisting of hydrogen, fluorine, chlorine and bromine and y is an integer from 1 to 6;
   b) heating said mixture, and;
   c) recovering a second mixture comprising 1,1-difluoroethane.

2. The process of claim 1 wherein said heating is carried out at a temperature of from about 30° C. to 160° C.

3. The process of claim 1 wherein said alkali metal halide is selected from the group consisting of NaCl, NaF, KCl and KF.

4. The process of claim 1 wherein said tin catalyst is selected from the group consisting of $SnCl_4$, $SnBr_4$, $SnCl_3F$, $SnCl_2F_2$, $SnClF_3$, $SnF_4$, $SnCl_2O$, $SnF_2O$, $SnClFO$, $Sn(CH_3)_4$, $OSn(C_2H_5)_2$ and $SnCl_2(CH_3)_2$.

5. The process of claim 1 wherein said saturated halogenated hydrocarbon is selected from the group consisting of methylene chloride, 1,2-dichloroethane, 1,1-dichloroethane, 1-chloro-1-fluoroethane, and 2,2-dichloro-1,1,1-trifluoroethane.

6. The process of claim 1 wherein said catalyst system contains from about 0.001 to 2 moles of said alkali metal halide per mole of said tin catalyst.

7. The process of claim 1 wherein the mole ratio of said saturated halogenated hydrocarbon to said tin catalyst is from about 0.001 to 5.

8. The process of claim 1 wherein:
   a. said alkali metal halide is selected from the group consisting of NaCl, NaF, KCl and KF;
   b. said tin catalyst comprises at least one member from the group consisting of $SnCl_4$, $SnBr_4$, $SnCl_3F$, $SnCl_2F_2$, $SnClF_3$, $SnF_4$, $SnCl_2O$, $SnF_2O$, $SnClFO$, $Sn(CH_3)_4$, $OSn(C_2H_5)_2$ and $SnCl_2(CH_3)_2$, and;
   c. said catalyst system contains from about 0.001 to 2 moles of said alkali metal halide per mole of said tin catalyst.

9. The process of claim 8 wherein said saturated halogenated hydrocarbon is selected from the group consisting of methylene chloride, 1,2-dichloroethane, 1,1-dichloroethane, 1-chloro-1-fluoroethane, and 2,2-dichloro-1,1,1-trifluoroethane and the mole ratio of said saturated halogenated hydrocarbon to said tin catalyst is from about 0.001 to 5.

10. The process of claim 1 wherein said process is a continuous process.

* * * * *